(12) United States Patent
Weinberg et al.

(10) Patent No.: US 6,324,428 B1
(45) Date of Patent: Nov. 27, 2001

(54) IMPLANTABLE MEDICAL DEVICE HAVING AN IMPROVED ELECTRONIC ASSEMBLY FOR INCREASING PACKAGING DENSITY AND ENHANCING COMPONENT PROTECTION

(75) Inventors: Alvin Weinberg, Moorpark; Sergiu Silvian, La Crescenta; Min-Yaug Yang, Irvine, all of CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/281,424

(22) Filed: Mar. 30, 1999

(51) Int. Cl.⁷ ................................... A61N 1/375
(52) U.S. Cl. .................................... 607/36
(58) Field of Search .................. 607/1, 2, 9, 36

(56) References Cited

U.S. PATENT DOCUMENTS

| 4,041,956 | * | 8/1977 | Purdy et al. ...................... 128/419 |
| 4,616,655 | | 10/1986 | Weinberg et al. ................. 128/419 |
| 5,222,014 | | 6/1993 | Lin ..................................... 361/414 |
| 5,282,841 | | 2/1994 | Szyszkowski .................... 607/36 |
| 5,470,345 | * | 11/1995 | Hassler et al. ................... 607/36 |
| 5,480,416 | | 1/1996 | Garcia et al. .................... 607/36 |
| 6,026,325 | * | 2/2000 | Weinberg et al. ............... 607/36 |

FOREIGN PATENT DOCUMENTS

| 000528393 | * | 2/1993 | (EP) .................................. 607/36 |
| 147850 | | 6/1989 | (JP) . |

* cited by examiner

Primary Examiner—William E. Kamm

(57) ABSTRACT

An implantable cardiac stimulation device having an improved multi-level electronic module is disclosed. The multi-level module comprises at least two stacked internal substrates for mounting electronic components within a confined region formed between the two stacked substrates. Placement of the two stacked substrates creates an opening establishing fluid communication between the confined region and an exterior of the electronic module. A polymer dielectric coating, such as parylene, is vapor deposited over the entire electronic module which penetrates the confined region via the opening. The parylene provides enhanced protection against dielectric breakdown between the electronic components and their interconnections thereby enabling smaller separation distances between the electronic components. The parylene also provides support for the electronic components and their interconnections while acting as a moisture barrier and a particle getter.

7 Claims, 4 Drawing Sheets

IMPLANTABLE MEDICAL DEVICE HAVING AN IMPROVED ELECTRONIC ASSEMBLY FOR INCREASING PACKAGING DENSITY AND ENHANCING COMPONENT PROTECTION

FIELD OF THE INVENTION

This invention relates generally to improvements in the packaging of electronic components suitable for implantable medical devices. More particularly, this invention relates to methods and apparatus for constructing a multi-level high density electrical package which is optimally protected from dielectric breakdown, moisture, and other contaminants.

BACKGROUND OF THE INVENTION

It will be appreciated that the invention has utility with respect to improvements in electronic packaging that may be suitable for many applications. However, the present invention has some unique features which maximize utilization of space within an implantable medical device and provide enhanced protection for internal electronic components.

Implantable medical devices of the type having electrical circuit components are well known in the medical arts. In one particularly common form, the implantable device comprises a pacemaker, or other stimulation device, having an appropriate electrical power supply and related control circuitry for use in electrically stimulating a patient muscle, such as the heart. Such a pacemaker commonly includes a hermetically sealed case or housing within which a power supply and control circuitry are placed, in combination with one or more conductive pacemaker leads extending from the housing to the selected muscle structure within the patient.

Signals into and out of the circuitry within the housing of a common stimulation device are coupled through the housing by means of feedthrough terminals of various types known in the art. Examples of such stimulation devices may be found in commonly assigned U.S. Pat. No. 5,282,841 to Szyszkowski.

As is apparent from the Szyszkowski patent, the size of the housing is dependent upon that required to house both the battery and the electronic control circuitry constituting the pulse generator. A major factor which drives the electronic control circuit design is the need to fit large, generally rectangular or cylindrical components into a physiologically-shaped, curved housing. Of course, efforts are continually being made to minimize the size of the housing, and thus the size of the internal components, while maximizing the effectiveness of the device.

The control circuitry of implantable stimulation devices is often a multi-level hybrid circuit module. The multi-level module is ordinarily designed to achieve a low-volume configuration to facilitate placement within the limited confines of an associated device housing. Multi-level circuit modules may contain separate vertically stacked substrates, i.e., platforms, having individual circuit components mounted on the substrates. A protective cover, or lid, is typically placed over any exposed electronic circuitry of the multi-level module.

There have been many approaches documented in prior art publications for constructing a multi-layer, or three-dimensional, circuit module used in implantable devices. For example, in U.S. Pat. No. 5,222,014 issued to Lin, and Japanese publication No. 1-147850 issued to Kuwabara, independent circuit platforms are stacked above a substrate to create the multi-level structures. In each case a lid may be placed over the structure to protect the underlying circuitry.

As the electronic circuit modules of implantable medical devices become more complex and more densely configured, design constraints for closely configuring the associated electronic components become ever more significant. In particular, the electronic components must be free of errant particles and other ionic contaminants which could interfere with the electronic circuitry or damage miniature wirebond connections.

Some methods of sealing pacemaker devices and the like include those disclosed in U.S. Pat. No. 5,480,416 issued to Garcia et al., and U.S. Pat. No. 4,616,655 issued to Weinberg et al. In the Garcia et al. patent, an electrically insulative coating is applied over the entire surface of the implantable device case. In Weinberg et al., however, the electronic pulse generator of a cardiac pacer includes an internal chip carrier housing which is hermetically sealed.

In a high voltage system, such as an implantable cardioverter-defibrillator, the packaging density of the electronic components within an implantable device module is largely determined by the dielectric properties of the material separating the components. Previous methods of insulating electronic components have including using air as a natural dielectric, or as disclosed in the Lin patent, an encapsulating molding compound may be placed over the various electronic components for protection. Such methods achieve a certain level of dielectric breakdown protection which may not be suitable for the increased packaging density found in the most advanced implantable medical devices.

The present invention represents an improvement over previous implantable medical devices which allows for increased packaging density and improved protectability of internal electronic components.

SUMMARY OF THE INVENTION

The present invention comprises an implantable medical device having a multi-level electronic module which may be characterized by at least two stacked internal substrates for mounting electronic circuits. The electronic module has a protective lid for protecting the substrates and an external interconnect structure mounted on the lid which is also capable of mounting electronic components.

The electronic components of the present invention comprise a hybrid assembly including a first substrate for supporting passive and active electronic circuitry components and their electrical interconnections. The first substrate may be formed with a cavity on a first side which defines a depressed surface for mounting electronic components thereon.

The present invention further includes an intermediate substrate mounted on the first side of the first substrate, the intermediate substrate having a lower surface facing the depressed surface and having an upper surface. Both surfaces of the intermediate substrate are capable of supporting electronic circuitry including active and passive components and their electrical interconnections.

Advantageously, one or more air gaps are maintained between the first and intermediate substrates, such as along the edges, to establish fluid communication between the electronic components mounted on the first substrate and the upper surface of the intermediate substrate. A lid is placed over the substrates to protect the active components on the first and intermediate substrates. The lid is further capable of supporting and interconnecting the large, typically externally-mounted device components (such as inductors, telemetry coils, and a reed switch) to the hybrid assembly.

The lid is mounted on the first side of the first substrate overlying the upper surface of the intermediate substrate and has one or more notches for establishing fluid communication between an exterior portion of the lid and the underlying substrates. A protective coating, such as parylene, or other suitable polymer material, is vapor deposited over the entire hybrid assembly. The presence of the lid notches and the substrate air gaps allows for uniform coating of the underlying circuit components mounted on the first and intermediate substrates. Due to the high dielectric breakdown properties of materials such as parylene, increased packaging density of the circuit components can be maintained. The deposited coating also helps support the miniature electronic components and the delicate wirebond connections between such components. In addition, the parylene coating provides protection against moisture and contaminants interfering with electronic operations.

While the embodiment described above includes a vertically oriented hybrid circuit assembly, it is within the spirit of the invention to apply the principles of parylene coating, and in particular parylene coating throughout multi-cavity structures, to other assembly configurations.

Accordingly, a primary feature of the present invention is to provide improvements in the achievable packaging density of electronic components of a circuit assembly.

Another feature of the invention is to provide an improved method for protecting internal electronic components of an electronic package against moisture and contaminant particles.

A further feature of the invention is to provide additional support and adhesion of miniature electrical-interconnect wirebonds through application of a protective polymer coating.

Still another feature of the present invention is to provide a high density electronic package for an implantable medical device which is of minimal size but of maximized effectiveness.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate certain of the embodiments of the invention, and together with the description, serve to explain the principles of the invention in general terms. Like numerals refer to like parts throughout the disclosure.

DETAILED DESCRIPTION OF THE PREFERRED EMBODIMENTS

Figure 1:
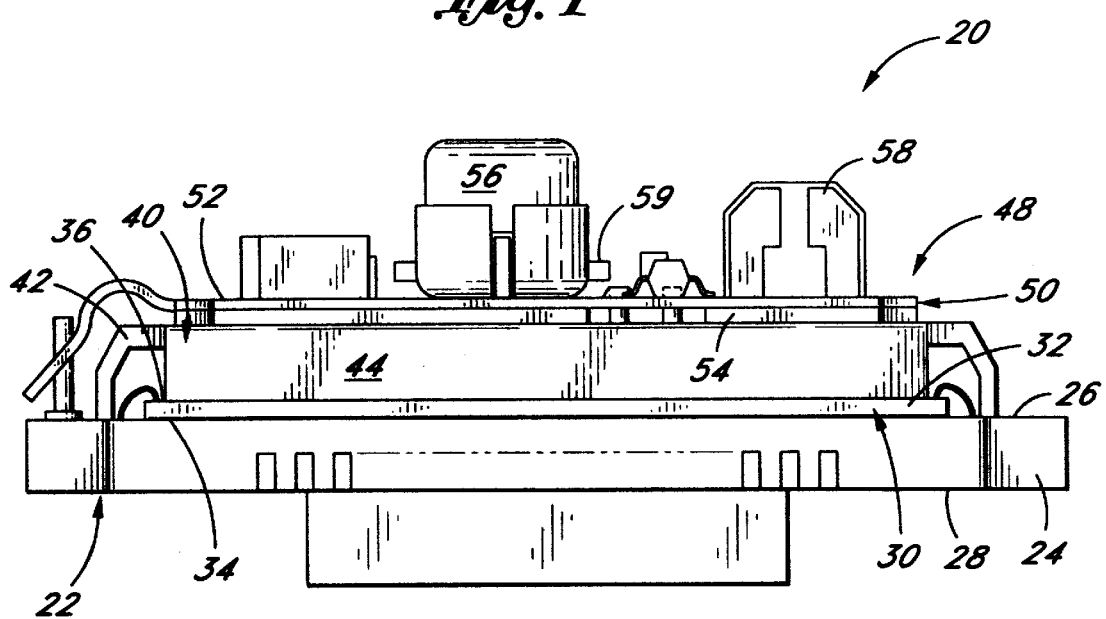
FIG. 1 is a side elevation view of a high density electronic circuit module embodying the invention.

Referring initially to FIG. 1, there is illustrated a multi-level high density electronic module 20 embodying the present invention. The module is of a type useful for controlling functions of electronic devices, for example, regulating the cardiac pulses of a difibrillator unit delivered to a host patient. The invention is particularly suited for implantable medical devices such as pacemakers and defibrillators, but the technology presented in this disclosure can be used in any electronic device application especially those where space constraints are of concern.

The multi-level module 20 comprises a first hybrid circuit assembly 22 including a first, or base, substrate 24 having first and second opposed surfaces, 26, 28, respectively. The module 20 further comprises an intermediate hybrid circuit assembly 30 including an intermediate substrate 32 mounted on the first opposed surface 26 of the first substrate 24. The intermediate substrate 32 has a lower surface 34 placed atop the first opposed surface 26 of the first substrate, and an upper surface 36 facing away from the opposed surface 26. A protective lid 40 is placed over the first and second hybrid circuit assemblies 22 and 30. The lid 40 includes a pair of opposed laterally extending legs 42 and a pair of opposed longitudinally extending legs 44. The legs 42, 44 are used, respectively, for mounting the lid 40 on the first surface 26 of the first substrate 24 and on the upper surface 36 of the intermediate substrate 32 so as to be spaced from and overlying the upper surface 36 of the intermediate substrate 32 and the electronic components mounted on that upper surface 36.

An externally mounted interconnect structure 48 includes an outer substrate 50 having outer and inner opposed surfaces, 52, 54, respectively, and is suitably mounted on the lid 40, as by adhesive or other means. The outer substrate 50 supports electronic circuitry on its upper surface 52 comprised of electronic components such as an inductor 56, a telemetry coil 58, and a reed switch 59. Advantageously, these electronic components 56, 58, 59 may be mounted in such a manner that they fit (heightwise) in the curved portion of an implantable device housing, thereby maximizing the utilization of space in the housing.

Figure 2:
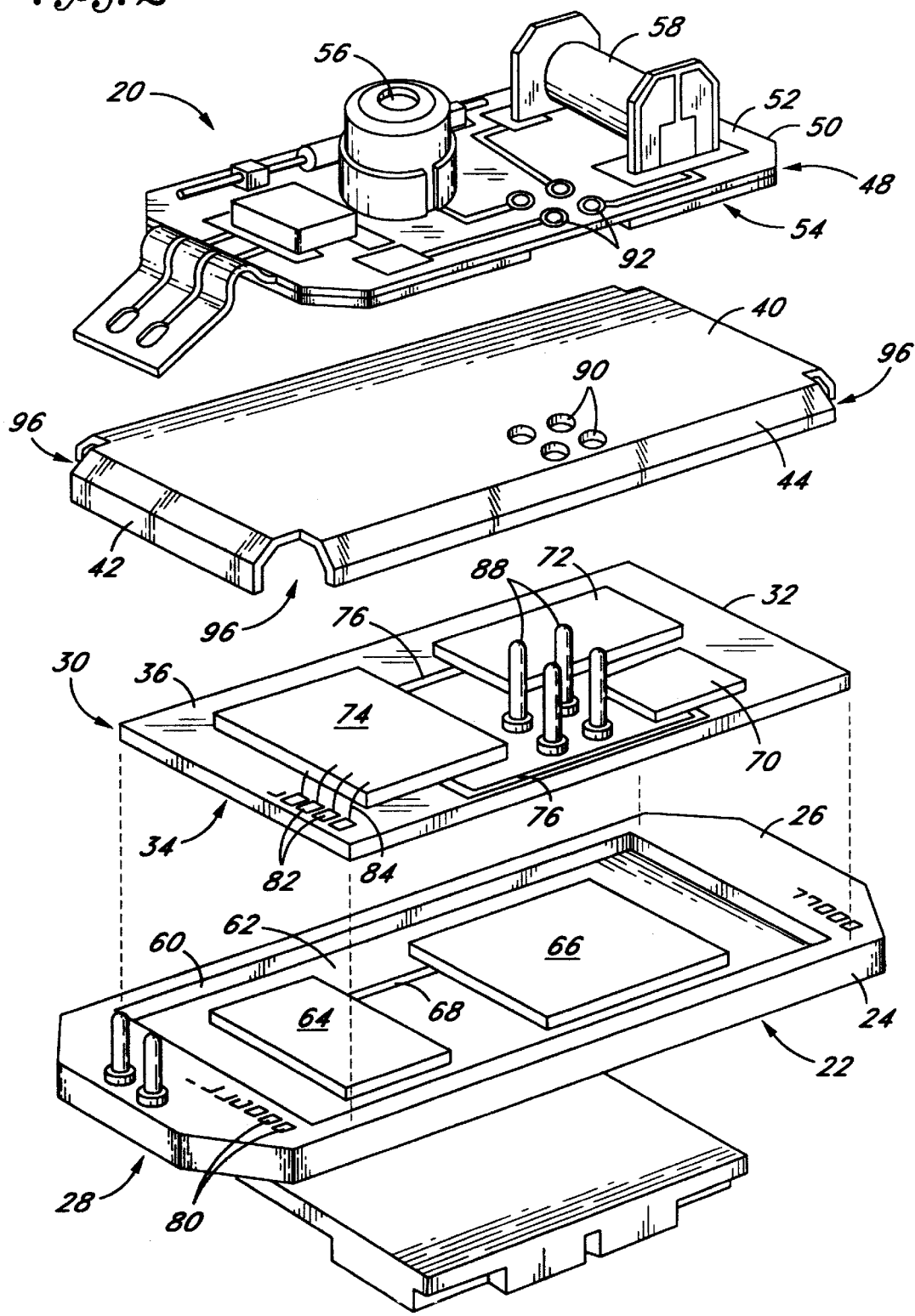
FIG. 2 is an exploded perspective view of the high density electronic circuit module illustrated in FIG. 1.

Referring now to FIG. 2, an exploded perspective view of the module 20 is shown which depicts in more detail the features of the present invention. In particular, it can be seen from FIG. 2 that the first substrate 24 of the first hybrid assembly 22 is formed with a cavity 60 into the first opposed surface 26 defining a depressed surface 62. The surface 62 has various electronic circuitry mounted thereon including components 64, 66, such as integrated circuits, and electrical interconnections 68 therebetween.

As with the first substrate 24, the intermediate substrate 32 of the intermediate hybrid assembly 30 has mounted thereon electronic components 70, 72, 74 and electrical interconnections 76 among the components. In the context of an implantable medical device, such as a pacemaker or defibrillator, the intermediate hybrid assembly 30 may be a digital hybrid assembly and the first hybrid assembly 22 may be an analog hybrid assembly.

Electrical interconnection between the first substrate 24 and the intermediate substrate 32 is achieved by wirebonds (shown in FIG. 3) which are in vertical registration between a plurality of wirebond pads 80 on the first substrate 24 and a plurality of wirebond pads 82 on the intermediate substrate 32. Wirebonds are also used to interconnect the various circuit components to the substrate upon which they are mounted. For example, wirebonds 84 connect the integrated circuit component 74 to the wirebond pads 82 of substrate 32.

Additionally, a plurality of upstanding pin terminals 88 are mounted, as by brazing, on the upper surface 36 of the intermediate substrate 32. The pin terminals 88 have electrical continuity with specific ones of the electronic components 72, 74 mounted on the intermediate substrate 32 by means of internal tracing or vias (not shown) within the substrate 32. The pin terminals 88 extend through apertures 90 of the lid 40 for contact with terminals 92 of the outer substrate 50. In this manner, the components 70, 72, 74 on the intermediate hybrid assembly 30 are electrically connected with the components 56, 58, and others, as desired, on the outer substrate 50 mounted on the lid 40.

As commonly used in implantable medical devices, certain electronic components of the hybrid module 20 will operate under relatively high-voltages. Accordingly, design guidelines are necessary for determining separation distances between conductors, wirebonds, and other components to prevent dielectric breakdown, i.e., arcing. The dielectric breakdown in air is approximately 75–80 volts/mil. Current high-voltage hybrid design guidelines, common to one of ordinary skill in the art, require that the separation distance for dielectric breakdown be approximately doubled. Thus, the design separation for electronic leads in a 1000 volt system using air as a dielectric is 25 mils.

An increase in packaging density of the hybrid module 20 can be obtained by using a dielectric with a high breakdown voltage. Although many dielectric materials have higher breakdown voltages than air, not all are suitable for application within an implantable medical device. For example, the dielectric coating must be compatible with the electronic components. Furthermore, the dielectric coating cannot damage any of the miniature components, or wirebond connections, through its application or the curing process. The present invention improves packaging density of electronic components by depositing a suitable polymer coating, such as parylene, over the entire hybrid assembly 20 including the internal components.

Deposition of parylene provides a much increased breakdown voltage with each one-mil thick layer providing approximately 5000 volts of breakdown protection. Through the use of parylene, the required design separation of electronic components can be significantly reduced without increasing the possibility of arcing between components. The use of parylene coating on hybrid circuits also acts as a particle getter and provides a barrier against moisture and ionic contaminants. Additionally, a parylene coating will also provide support for and improve the adhesion of wirebonds.

Application of parylene and other polymers is typically performed in a vapor deposition process. In accordance with the present invention, the parylene is applied to the assembled hybrid module 20. Accordingly, it is important that the parylene reach and be deposited upon all of the internal electronic components affixed within the hybrid module 20. To ensure that the parylene is uniformly deposited within the hybrid module 20, the module is uniquely designed to ensure fluid communication between the first hybrid assembly 22 and the intermediate hybrid assembly 30.

Referring still to FIG. 2, the dimensions of the intermediate substrate 32 are generally similar to that of the first substrate 24, except that the intermediate substrate 32 is shorter on one or two opposing sides of the cavity 60. Placement of the substrate 32 over the substrate 24 thus leaves a portion of the cavity 60 uncovered by the substrate 32 establishing fluid communication between the cavity 60 and the intermediate hybrid assembly 30. Additionally, fluid communication is established between the intermediate substrate 32 and the exterior of the module 20 through a series of notches 96 formed at the corners of the lid 40. Vapor deposition of parylene over the entire exterior surface and interior surface of the module 20, including the electronic components mounted therein, is achieved when the parylene passes through the notches 96 and into the first and intermediate hybrid assemblies, 22, 30. The means by which fluid communication is established throughout the hybrid module 20 can best be seen in conjunction with FIGS. 3 and 4 which depict the hybrid module 20 in section.

Figure 3:
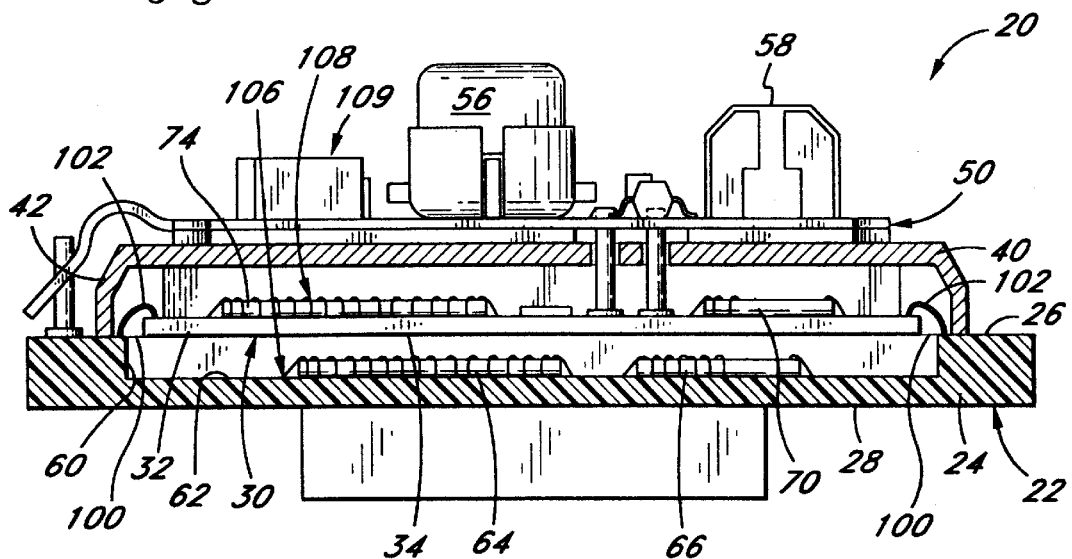
FIG. 3 is a side elevation view, in section, of a preferred embodiment of the high density electronic circuit module illustrated in FIG. 1.

Referring initially to FIG. 3, the dimensional relationship of the intermediate substrate 32 is seen to be shorter than the first substrate 24. More specifically, the intermediate substrate 32 does not extend longitudinally the full length of the cavity 60, thereby resulting in openings, or apertures, 100 between the cavity 60 and the intermediate hybrid assembly 30. The openings 100 formed between the first and intermediate hybrid assemblies 22, 30, of the module 20 enable vapor deposition of a suitable polymer coating (e.g., parylene) for protection of the electronic components therein. The coating is applied over all of the surfaces within the cavity 60, for example surface 106, the surfaces throughout the intermediate hybrid assembly 30, for example surface 108, and over the surfaces on the external components such as surface 109. Also, as mentioned previously in connection with FIG. 2, miniature wirebonds 102 make electrical connection between the intermediate substrate 32 and the first substrate 24.

Figure 4:
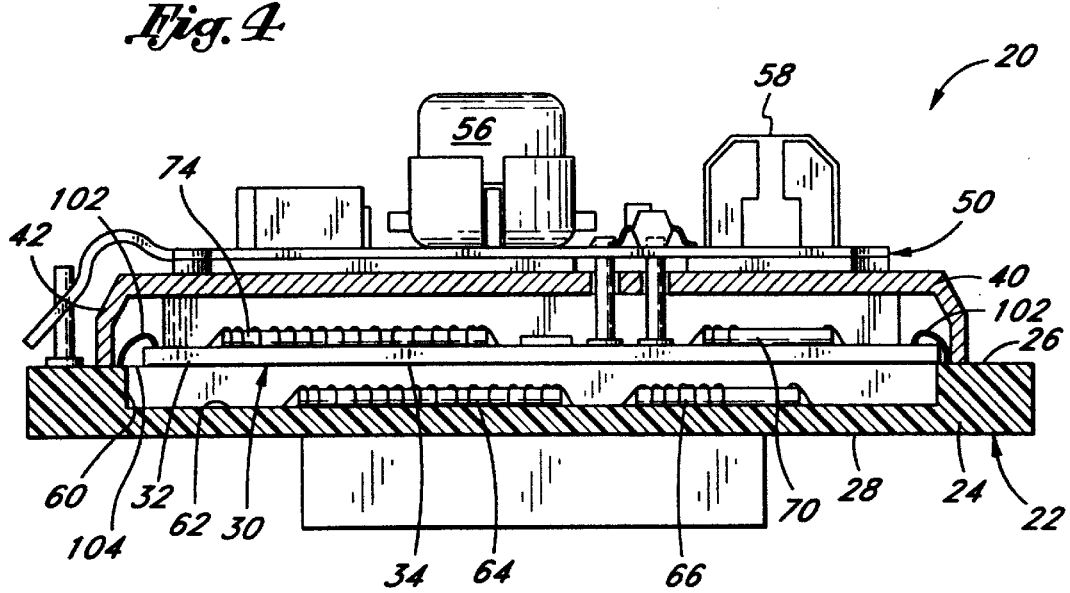
FIG. 4 is a side elevation view, in section, of an alternative embodiment of the high density electronic circuit module illustrated in FIG. 3.

Referring now to FIG. 4, an alternative embodiment of the module 20 is shown in cross section whereby the intermediate substrate 32 is of sufficient length to cover the cavity 60 on all sides except one. This results in a single opening 104 through which vapor deposition of parylene may flow to cover the internal components placed within the cavity 60. The opening 104 of FIG. 4 is seen as residing along an edge near a longitudinal end portion of the cavity 60.

Alternatively, or in addition to the openings 100, 104 maintained along the edges of the substrate 32 as seen in FIGS. 3 and 4, other openings may be formed directly through the intermediate substrate 32 or at any other point between the assemblies 22, 30, as may be required due to design constraints of the hybrid module 20. Moreover, the cavity defined between the first and intermediate substrates may be formed within the intermediate substrate whereby the intermediate substrate attaches to a flat first substrate along a periphery and the opening is created somewhere along the periphery or within the intermediate substrate.

Figure 5:
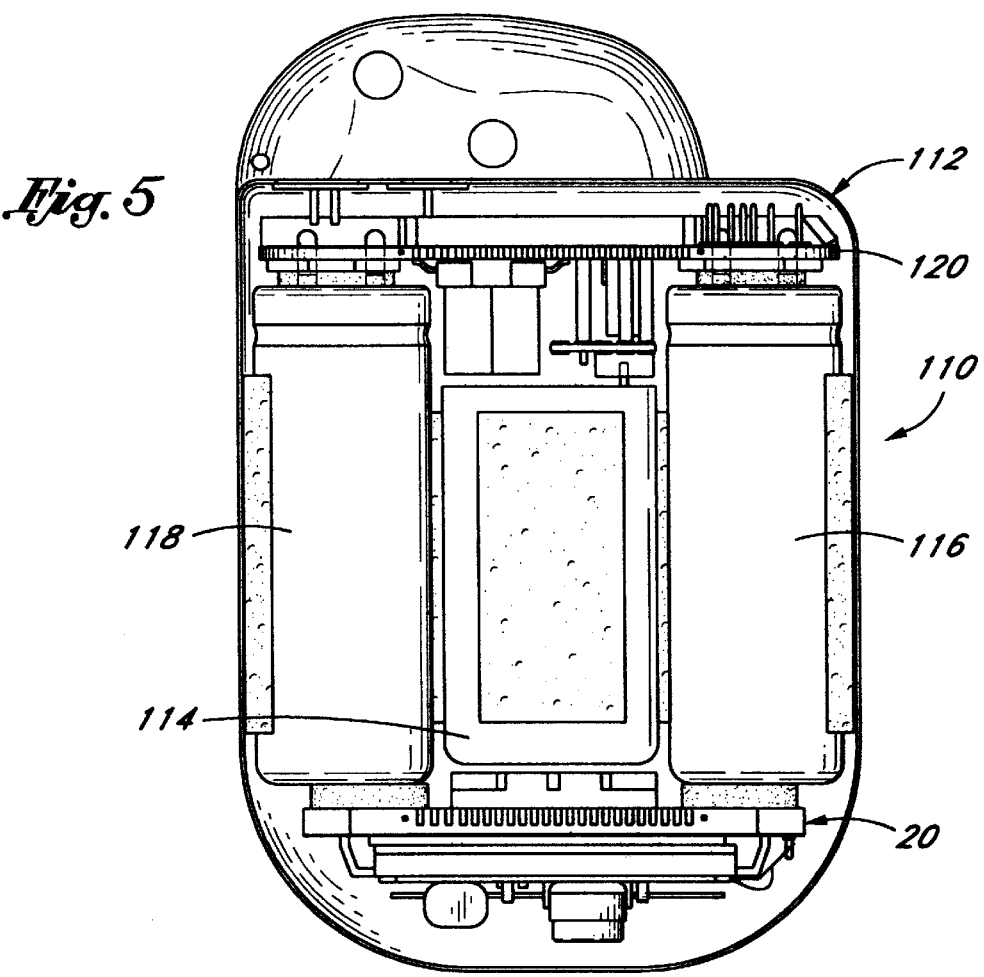
FIG. 5 is a plan view of an implantable stimulation device depicting the configuration of the assembled internal components in accordance with a preferred embodiment.

FIG. 5 shows one embodiment of the present invention as an implantable cardioverter defibrillator (ICD) 110. An internal view of the ICD 110 is shown in FIG. 5 in final assembled form which consists of a housing 112, a battery 114, charge capacitors 116 and 118, a high-voltage electronics package 120, and the electronic module 20. The principles of the present invention may be equally applied to any or all of the components of the ICD 110 including the high-voltage electronics package 120. For a complete description of the ICD, see U.S. Pat. No. 5,471,313, which patent is hereby incorporated by reference in its entirety.

The housing 112 is physiologically-shaped and the electronic module 20 is shown in the lower curved portion of the housing 112. The configuration of the module 20 is advantageously optimized to reduce the required volume of the housing 112.

The electronic module 20 is a control module which performs cardiac pacing and sensing functions for determining when a high voltage discharge to a host patient is warranted. The basic design and operation of a typical cardioverter-defibrillator are common to one of ordinary skill in the art and will not be discussed in detail in accordance with a preferred embodiment of the present invention.

Figure 6:
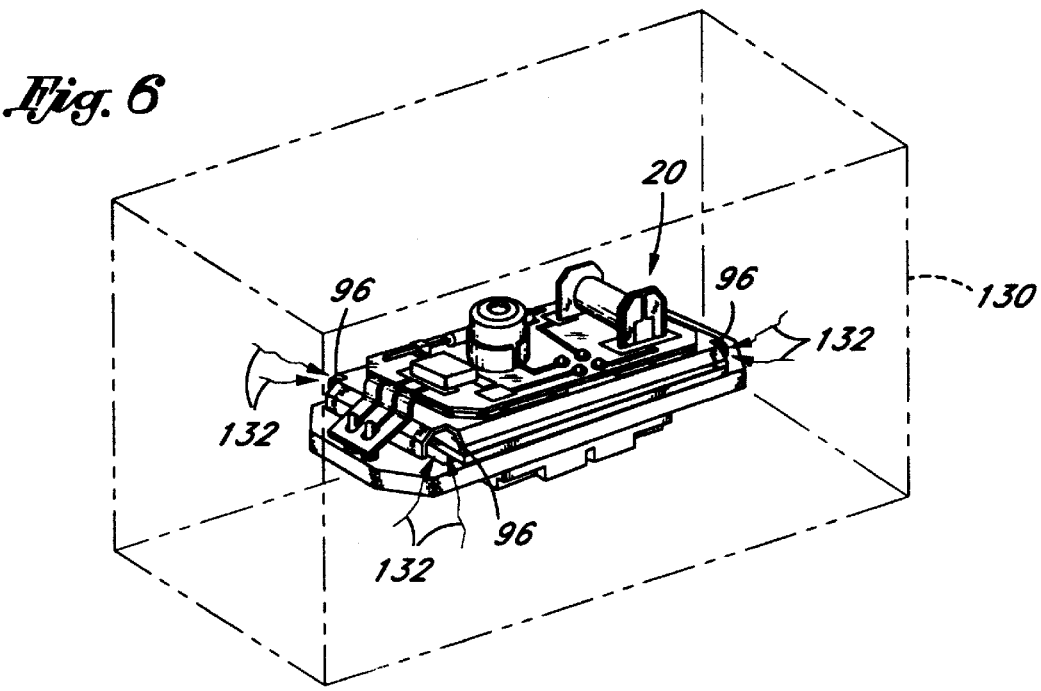
FIG. 6 is a perspective view of a vapor deposition chamber and an associated high density electronic circuit module undergoing a parylene coating process.

Depicted in FIG. 6 is the hybrid circuit module 20 in accordance with the present invention situated within a chamber 130 used for the vapor deposition of a polymer coating. In accordance with the prior discussion herein, a polymer vapor such as parylene, represented by the lines 132, flows throughout the chamber 130 and passes through apertures formed by the notches 96 of the lid 40. In this manner the applied polymer coats the exterior and interior surfaces, including the electronic components, of the module 20. The module 20 may also be polymer coated by placing the entire cardiac stimulation device 110, having a portion of the outer cover removed (as shown in FIG. 5), within the chamber 130. This allows coating of all exposed internal surfaces within the cardiac stimulation device 110.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. An implantable cardiac stimulation device for stimulating a patient's heart, comprising:
   a housing for implantation in the human body and for containing electronic components of the stimulation device therein;
   a multi-level high density electronic module mounted within the housing for controlling pulse generating functions of the stimulation device, the electronic module comprising:
   a first substrate having a cavity formed therein for mounting within the cavity electronic circuitry including components and electrical interconnections therebetween;
   an intermediate substrate having first and second opposed surfaces, the intermediate substrate mounted in vertical registration above the first substrate wherein the first opposed surface is placed atop the cavity formed in the first substrate, and wherein the first opposed surface is positioned to form an opening establishing a communication path for fluid between the cavity and the second opposed surface of the intermediate substrate; and
   wherein, the opening between the cavity and intermediate substrate permits fluid comprising a vaporized polymer material, to penetrate the interior of the cavity for coating the electronic circuitry mounted on the first substrate within the cavity.

2. The implantable cardiac stimulation device, as set forth in claim 1, wherein placement of the intermediate substrate atop the first substrate leaves an end portion of the cavity uncovered and the opening is formed along an edge of the cavity at the end portion.

3. The implantable cardiac stimulation device, as set forth in claim 1, wherein the opening formed by the positioning of the intermediate substrate atop the first substrate is characterized by first and second apertures created at opposite ends of the cavity.

4. The implantable cardiac stimulation device, as set forth in claim 1, wherein the opening is formed within the intermediate substrate.

5. The implantable cardiac stimulation device, as set forth in claim 1, wherein the high-density electronic module further comprises a protective lid mounted atop the first and intermediate substrates, the lid having apertures formed therein for establishing fluid communication between an exterior surface of the lid, the intermediate substrate, and the cavity.

6. The implantable cardiac stimulation device, as set forth in claim 1, wherein the high-density electronic module further comprises a layer of polymer material deposited over the intermediate and first substrates and within the cavity.

7. The implantable cardiac stimulation device, as set forth in claim 6, wherein the polymer material is parylene.

* * * * *